United States Patent [19]

Colvin et al.

[11] Patent Number: 5,025,220

[45] Date of Patent: Jun. 18, 1991

[54] CONTINUOUS MEASUREMENT OF THE ABSOLUTE CONDUCTIVITY OF A LIQUID

[75] Inventors: Alex D. Colvin, Oak Park; Daniel J. Graham, Farmington; Joseph C. Cassatta, Taylor, all of Mich.

[73] Assignee: Ford Motor Company, Dearborn, Mich.

[21] Appl. No.: 410,772

[22] Filed: Sep. 21, 1989

[51] Int. Cl.⁵ ............................................. G01N 27/02
[52] U.S. Cl. ..................................... 324/449; 324/444
[58] Field of Search ............... 324/449, 444, 446, 441, 324/439, 700, 71.2, 442

[56] References Cited

U.S. PATENT DOCUMENTS

| | | | |
|---|---|---|---|
| 2,842,736 | 7/1958 | Heyd et al. | 324/444 |
| 3,731,187 | 5/1973 | Hausler et al. | 324/700 |
| 3,848,187 | 11/1974 | Rohrback et al. | 324/700 |
| 3,879,657 | 4/1975 | Nystuen et al. | 324/30 R |
| 3,946,309 | 3/1976 | Roughton et al. | 324/64 |
| 4,284,951 | 8/1981 | Dahl et al. | 73/304 R |
| 4,362,994 | 12/1982 | Goldsmith et al. | 324/449 |
| 4,365,200 | 12/1982 | Goldsmith | 324/449 |
| 4,654,598 | 3/1987 | Arulanandan et al. | 324/449 |
| 4,682,113 | 7/1987 | Barben, II | 324/441 |
| 4,706,015 | 11/1987 | Chen | 324/64 |
| 4,751,466 | 6/1988 | Colvin et al. | 324/449 |
| 4,755,744 | 7/1988 | Moore et al. | 324/700 |
| 4,786,875 | 11/1988 | Carll | 324/444 |
| 4,808,931 | 2/1989 | Ling | 324/449 |
| 4,833,413 | 5/1989 | Head | 324/446 |

Primary Examiner—Kenneth Wieder
Assistant Examiner—Maura K. Regan
Attorney, Agent, or Firm—Paul Godwin; Roger L. May

[57] ABSTRACT

A method and apparatus for measuring the electrical conductivity of a liquid comprises an electrically insulating housing through which the liquid flows, and four electrodes inserted into the path of the liquid flowing through the housing. The first and third electrodes are current electrodes and the second and fourth electrodes are voltage electrodes. An AC current is injected into the first current electrode and exits at the second current electrode, with the resulting AC voltage across the voltage electrodes being measured. The first current electrode is driven to maintain a constant value of AC voltage on the voltage electrodes while measuring the current flow in the second current electrode which is representative of the electrical conductivity of the liquid. A DC bias voltage source is provided and is coupled to each of the electrodes by a resistor and a capacitor to prevent coating or plating of the electrodes. The method and apparatus permit continuous monitoring of the absolute conductivity of a liquid.

9 Claims, 1 Drawing Sheet

CONTINUOUS MEASUREMENT OF THE ABSOLUTE CONDUCTIVITY OF A LIQUID

BACKGROUND OF THE INVENTION

This invention relates to measuring the conductivity of a liquid and, more particularly, to an improved method and apparatus for continuously measuring the absolute conductivity of a production electrocoat paint wherein a bias voltage is imposed on electrodes of a conductivity measuring instrument to prevent fouling and repel the paint from the electrodes.

The conductivity of a solution such as paint is generally monitored using either one of two basic methods. The first method measures conductivity directly by maintaining a fixed voltage between two electrodes immersed in the solution so that the resulting current flow is directly proportional to the conductivity. In the second method, the electrodes may be supplied with a constant current flow so that the potential between them is directly proportional to the resistivity of the solution, which is the reciprocal of the conductivity.

It has been found in the industry that close control of production electrocoat paint conductivity is necessary for good paint coverage of a substrate, uniform coating thickness, and minimization of pinholes. High conductivity of the paint can cause excessive paint film thickness and low conductivity can cause poor "throwing power." Also, if the conductivity of the paint becomes extremely high, ultrafilters can plug, requiring excessive maintenance. Due to the nature of cathodic or anodic electrocoat processes, most sensors for instruments currently available become fouled with paint. Fouling occurs because the voltage levels of the electrodes allow electrocoat paint solids to electrically plate onto the surfaces of the electrodes.

The present invention is directed to an improvement to the electrical conductivity measuring instrument of U.S. Pat. No. 4,751,466 for preventing paint from plating on the electrodes of the probe. This patent discloses an instrument for measuring the electrical conductivity of a liquid passing through a nonconducting tubular probe by means of four electrodes which are inserted into the probe and metering circuitry associated with the probe. An AC voltage is imposed on the first electrode such that current is injected into the liquid flowing through the probe with the current passing to the third electrode, both the first and the third electrodes being of low impedance for passing current through the liquid. The voltage is then measured across the second and fourth electrodes with the fourth electrode being grounded to shield the probe from any ground currents such that the current due to conduction through the liquid flowing in the probe is correctly measured.

However, problems still exist in that electrodes have a tendency to eventually become coated with the paint or other liquid being measured. These coatings can introduce a substantial impedance across the interface between the electrode and the liquid solution. This affects the accuracy of the conductivity reading by indicating a much lower conductivity value than is accurate for the liquid bath. This coating or buildup on the electrodes also necessitates periodic interruptions to permit inspection and cleaning of the electrodes. Hence, it would be desirable to provide a system for measuring the electrical conductivity of a liquid wherein a coating does not buildup on electrodes of the system which would be particularly applicable to measuring the electrical conductivity of an electrocoat paint without buildup of paint solids on the electrodes.

SUMMARY OF THE INVENTION

The present invention solves the electrode coating problem of the prior art by providing a bias voltage on each of four electrodes by means of coupling capacitors and associated bias resistors. With the electrodes thus biased, an electrically conductive liquid, for example electrocoat paint, will not coat or be plated onto the electrodes. A positive bias is provided for cathodic electrocoat paint while a negative bias is provided for anodic electrocoat paint. The voltage bias impressed on the electrodes keeps the paint from being coated thereon and may even remove paint from electrodes which are already fouled. In addition, the voltage at the first electrode is monitored and if the voltage exceeds certain thresholds, a warning signal is activated to warn personnel of excess electrode fouling, which can occur if the instrument is emptied such that paint can dry on the electrodes.

In accordance with one aspect of the present invention, a method for measuring the electrical conductivity of a liquid comprises the steps of: forming an electrically insulating housing which defines a path through which the liquid flows; inserting at least four electrodes into the path of the housing, two of the electrodes being current electrodes and two of the electrodes being voltage electrodes; measuring the AC voltage across the voltage electrodes; driving a first one of the current electrodes to maintain the AC voltage on the voltage electrodes at a constant value; measuring the current flowing in a second of the current electrodes to determine the electrical conductivity of the liquid; providing a DC bias voltage source; and, coupling the DC bias voltage source to the at least four electrodes to prevent coating or plating the electrodes.

The method of measuring the electrical conductivity of a liquid may also include the steps of: monitoring the drive voltage on the first current electrode; comparing the drive voltage to a defined voltage which corresponds to an acceptable level of electrode fouling; and, activating an alarm if the drive voltage exceeds the defined voltage. In the method of the present invention for measuring the electrical conductivity of a liquid, preferably the path defines a longitudinal axis, the at least four electrodes are spaced along the axis, and the current electrodes comprise first and third electrodes while the voltage electrodes comprise second and fourth electrodes.

In accordance with another aspect of the present invention, an instrument for measuring the electrical conductivity of a liquid comprises an electrically insulating housing which defines a path through which the liquid flows. At least four electrodes are inserted into the path of the housing, two of the electrodes being current electrodes and two of the electrodes being voltage electrodes. First sensing means measure the AC voltage across the voltage electrodes generated by AC drive means which drive a first one of the current electrodes to maintain the AC voltage on the voltage electrodes at a constant value. Second sensing means measure the current flowing in a second of the current electrodes to determine the electrical conductivity of the liquid. A DC bias voltage source is provided and circuit means couple the DC bias voltage source to the at least four electrodes to prevent coating or plating the electrodes.

In accordance with preferred embodiments, it is an object of the present invention to provide a method and apparatus for measuring the electrical conductivity of a liquid wherein sensing electrodes repel constituents of the liquid to prevent coating or plating of the electrodes; it is also an object of the present invention to provide a method and apparatus using electrodes for measuring the electrical conductivity of paint wherein coating or plating of paint solids onto the electrodes is prevented; and, it is another object of the present invention to provide a method and apparatus for measuring the electrical conductivity of paint wherein a bias voltage is imposed on sensing electrodes to prevent fouling of the electrodes and to repel paint solids from the electrodes.

Other objects and advantages of the invention will become apparent from the following description, the accompanying drawing, and the appended claims.

DETAILED DESCRIPTION OF THE INVENTION

Figure 1:
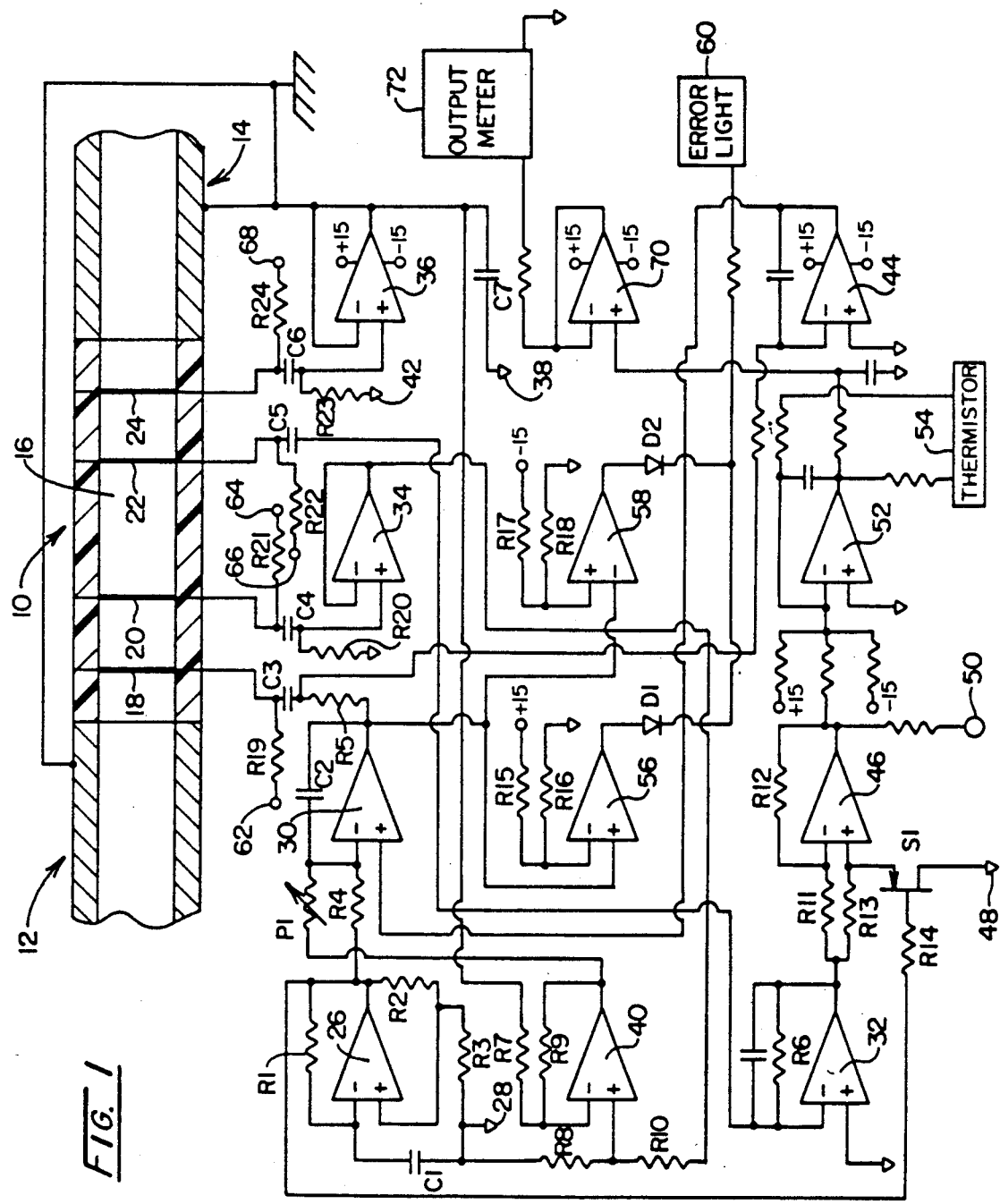
FIG. 1 is a schematic diagram illustrating a preferred embodiment of the present invention for measuring the continuous absolute conductivity of a liquid.

The conductivity instrument of the present invention comprises a tubular probe capable of continuously measuring the absolute conductivity of a liquid flowing therethrough. While the invention is generally applicable, it is particularly advantageous for continuously measuring the absolute conductivity of a production electrocoat paint bath. The invention includes a biasing arrangement for applying a bias voltage to four electrodes employed in the probe. Two of the electrodes introduce a current to the electrocoat paint while the other two electrodes measure the voltage across the electrocoat paint due to the current. Due to the nature of cathodic and anodic electrocoat processes, most sensors from instruments now available become fouled with paint as a result of the process. By utilizing a proper polarity bias voltage, the electrodes of the present invention repel paint solids, which makes the invention particularly well suited for the measurement of conductivity of electrocoat paint baths. Consequently, the invention permits accurate and continuous monitoring, without fouling, of the absolute conductivity in the electrocoat paint bath in which the conductance determines paint thickness and appearance of the final product. Additionally, the conductivity measuring instrument of the present invention incorporates an error light to warn if the electrodes have become coated with paint during system maintenance when air could enter the probe and cause the paint to dry on the electrodes. Finally, the instrument is temperature corrected so that valid readings can be obtained even if the paint bath temperature changes.

Referring now to the drawing, FIG. 1 shows a schematic diagram illustrating a preferred embodiment of an electrical conductivity measuring instrument in accordance with the present invention. FIG. 1 is shown partially in cross-section to illustrate the structure of a probe 10 which is preferably an electrically non-conducting tube connectable between any liquid carrying means such as metal pipes 12 and 14. The probe 10 carries any liquid 16 whose electrical conductivity is to be measured by the instrument. The probe 10 includes four electrodes 18, 20, 22, and 24, which are spaced substantially parallel to each other and substantially perpendicular to the longitudinal axis of the tube 10, though not necessarily extending around the entire circumference of the probe 10. Electrodes 18 and 22 are employed as a means for passing current, while electrode 22 is additionally employed as a means for measuring current. Electrodes 20 and 24 are employed as a means for measuring voltage generated across the liquid flowing through the probe 10 due to current driven through the liquid.

FIG. 1 illustrates a preferred embodiment of this invention for continuously measuring the absolute conductivity of a liquid. Referring now to the electrical portion of FIG. 1, reference number 26 refers to an oscillator amplifier which generates a fixed amplitude wave. The constant alternating current oscillator amplifier 26 along with resistors R1, R2, and R3 and capacitor C1 comprise a constant voltage generator circuit. Within the constant voltage generator circuit, resistor R1 connects the inverting input of oscillator amplifier 26 to the output of oscillator amplifier 26, while resistor R2 connects the output of oscillator amplifier 26 to the non-inverting input of oscillator amplifier 26. This non-inverting input of oscillator amplifier 26 is connected to a circuit ground 28 via resistor R3, while the inverting input of oscillator amplifier 26 is connected to the circuit ground 28 via capacitor C1.

Also shown in FIG. 1 is a current driver comprising an amplifier 30, resistors R4 and R5, and a capacitor C2. Stability is provided to the current driver, thereby avoiding high frequency oscillations, by the capacitor C2 which is connected between the output of the amplifier 30 and the inverting input of the amplifier 30. The output of the amplifier 30 supplies current to the current electrode 18 which flows through the liquid in the probe 10 to electrode 22 from which it is applied to a current to voltage converter amplifier 32. A current sampling resistor R6 is connected between the inverting input of amplifier 32 and the output of amplifier 32. The conduction current in the probe 10, i.e. the current flowing through the conductive liquid 16 whose electrical conductivity is being measured, is represented by the AC voltage output of amplifier 32.

The voltages at electrodes 20 and 24 of the probe 10 are buffered by the unity gain operational amplifiers 34 and 36, respectively, which operate as voltage followers. The voltage at electrode 24 is buffered by the unity gain operational amplifier 36, whose output is connected to the metal pipes 12 and 14 and to a circuit ground 38 through a capacitor C7. This arrangement allows the pipe 14 to shield the electrode 24. The two buffered outputs from the amplifiers 34 and 36 are subtracted using a difference amplifier 40 and its associated resistors R7, R8, R9, and R10, all of which comprise a differential amplifier. A resistor R7 connects the inverting input of the amplifier 40 and the output of the amplifier 36. The output of the amplifier 40 is connected to the inverting input of the amplifier 40 via a resistor R9, while the non-inverting input of the amplifier 40 is connected to a circuit ground 28 via resistor R8. Finally, a resistor R10 connects the non-inverting input of the amplifier 40 to the output of the amplifier 34. The output of the differential amplifier 40 and the oscillator amplifier 26 are summed in the current driver amplifier 30.

A resistor R4 is connected to the output of the oscillator amplifier 26 as well as being connected to the inverting input of the current driver amplifier 30. The output of the differential amplifier 40 is also connected to the inverting input of the current driver amplifier 30 via a gain potentiometer P1. This arrangement controls the current between the current electrodes 18 and 22 so as to produce a fixed fraction of the preferably square wave voltage between the two voltage sensing electrodes 20 and 24. This is provided since an excessively low voltage could reduce the sensitivity of the system and an excessively high voltage could cause bubbles to form on the current electrodes 18 and 22. A bias driver amplifier 44 is associated with the current driver amplifier 30 to center the square wave.

The preferred embodiment of the invention shown in FIG. 1 includes a synchronous detector comprising an amplifier 46, resistors R11, R12, R13, field effect transistor switch S1 and its input limiting resistor R14. The field effect transistor switch S1 either grounds or floats the non-inverting input of the synchronous detector amplifier 46. This provides a gain of −1 when the non-inverting input is grounded to a circuit ground 48 and a gain of +1 when the non-inverting input is floated. The alternating gain provides detection synchronized with the oscillator amplifier 26. A circuit output 50 is the circuit output of the synchronous detector and its voltage is proportional to the solution conductivity being measured. The use of the synchronous detector reduces electrical pickup, eliminates any electrode polarization, and eliminates effects due to DC currents passing through the probe 10.

Preferably, a temperature compensator amplifier 52 is associated with the synchronous detector amplifier 46. The output of the temperature compensator amplifier 52 is connected to a thermistor 54, providing temperature correction for the instrument so that valid readings can be obtained even if the temperature of the measured liquid changes. Additionally, the output of the temperature compensator amplifier 52 comprises a temperature corrected conductivity signal which is used to drive the meter driver amplifier 70 in the usual manner to in turn drive an output meter 72.

Also included in the preferred embodiment are error detector operational amplifiers 56 and 58. Error detector amplifier 56 has associated resistors R15 and R16 in addition to an associated diode D1. Likewise, error detector amplifier 58 has associated resistors R17 and R18 and an associated diode D2. An error indicating light 60 and the associated circuitry including the two operational amplifiers 56 and 58, the resistors R15, R16, R17, R18, and the diodes D1 and D2 are added to the circuit of the preferred embodiment to provide a warning when the drive voltage is insufficient to overcome electrode fouling. The drive voltage is automatically adjusted to overcome any build-up on the electrodes which might occur under certain process conditions, such as system maintenance, previously noted.

The instrument of the present invention is capable of continuously measuring the absolute conductivity of a liquid, and is especially advantageous when used to continuously measure the absolute conductivity of a production electrocoat paint bath. An important advancement of the circuit of the present invention is an electrode biasing arrangement for accomplishing the measurement without buildup of a coating on the electrodes. A positive bias voltage is impressed on each of the four electrodes 18, 20, 22, and 24 by means of coupling capacitors C3, C4, C5, and C6 and bias resistors R19, R20, R21, R22, R23, and R24 to repel cathodic electrocoat paint and prevent the paint from plating on the electrodes 18, 20, 22 and 24. Similarly, a negative bias voltage can be used with anodic paint. A bias voltage is provided at each of four connection points 62, 64, 66, and 68, corresponding to resistors R19, R20, R21, R22. A positive bias of +15 volts is provided at each of the connection points 62, 64, 66, and 68 for cathodic liquids while a negative bias of −15 volts is provided for anodic liquids. The bias impressed on the electrodes 18, 20, 22, and 24 by the improved circuit of the present invention prevents paint and other platable liquids from coating on the electrodes 18, 20, 22, and 24. Additionally, this circuit arrangement is capable of removing paint and other liquids from electrodes which are already fouled.

Having described the invention in detail and by reference to preferred embodiments thereof, it will be apparent that modifications and variations are possible without departing from the scope of the invention which is defined in the appended claims.

What is claimed is:

1. A method of measuring the electrical conductivity of a liquid comprising the steps of:
    forming an electrically insulating housing which defines a path through which the liquid flows;
    inserting at least four electrodes into the path of said housing, two of said electrodes being current electrodes and two of said electrodes being voltage electrodes;
    measuring the AC voltage across said voltage electrodes;
    driving a first one of said current electrodes to maintain the AC voltage on said voltage electrodes at a constant value;
    measuring the current flowing in a second one of said current electrodes to determine the electrical conductivity of the liquid;
    providing a DC bias voltage source; and
    coupling said DC bias voltage source to said at least four electrodes to prevent coating or plating said electrodes.

2. A method of measuring the electrical conductivity of a liquid as claimed in claim 1 further comprising the steps of:
    monitoring the drive voltage on said first current electrode;
    comparing said drive voltage to a defined voltage which corresponds to an acceptable level of electrode fouling; and
    activating an alarm if said drive voltage exceeds said defined voltage.

3. A method of measuring the electrical conductivity of a liquid as claimed in claim 1 wherein said path defines a longitudinal axis, said at least four electrodes are spaced along said axis, and said current electrodes comprise first and third electrodes and said voltage electrodes comprise second and fourth electrodes.

4. A method of measuring the electrical conductivity of a liquid as claimed in claim 1 wherein said DC bias voltage source provides a positive bias voltage for use with cathodic liquids, the conductivity of which is to be measured.

5. A method of measuring the electrical conductivity of a liquid as claimed in claim 1 wherein said DC bias voltage source provides a negative bias voltage for use with anodic liquids, the conductivity of which is to be measured.

6. An instrument for measuring the electrical conductivity of a liquid comprising:
- an electrically insulating housing which defines a path through which the liquid flows;
- at least four electrodes inserted into the path of said housing, two of said electrodes being current electrodes and two of said electrodes being voltage electrodes;
- first sensing means for measuring the AC voltage across said voltage electrodes;
- AC drive means for driving a first one of said current electrodes to maintain the AC voltage on said voltage electrodes at a constant value;
- second sensing means for measuring the current flowing in a second of said current electrodes to determine the electrical conductivity of the liquid;
- a DC bias voltage source; and
- circuit means for coupling said DC bias voltage source to said at least four electrodes to prevent coating or plating said electrodes.

7. An instrument for measuring the electrical conductivity of a liquid as claimed in claim 6 wherein said circuit means comprises a resistor and a capacitor for each of said electrodes.

8. An instrument for measuring the electrical conductivity of a liquid as claimed in claim 6 wherein said DC bias voltage source provides a positive bias voltage for use with cathodic liquids, the conductivity of which is to be measured.

9. An instrument for measuring the electrical conductivity of a liquid as claimed in claim 6 wherein said DC bias voltage source provides a negative bias voltage for use with anodic liquids, the conductivity of which is to be measured.

* * * * *